US00PP13879P29

(12) United States Plant Patent
Holtrop

(10) Patent No.: US PP13,879 P2
(45) Date of Patent: Jun. 17, 2003

(54) SNAPDRAGON PLANT NAMED 'DRAROSE'

(75) Inventor: Mathilde H. Holtrop, Aromas, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 10/059,367

(22) Filed: Jan. 31, 2002

(51) Int. Cl.[7] ..... A01H 5/00
(52) U.S. Cl. ..... Plt./322
(58) Field of Search ..... Plt./322

*Primary Examiner*—Kent Bell
(74) *Attorney, Agent, or Firm*—Jondle & Associates PC

(57) ABSTRACT

A snapdragon cultivar particularly distinguished by pink flowers, vigorous growth and basal branching.

1 Drawing Sheet

GENUS AND SPECIES

*Antirrhinum hybrida.*

VARIETY DENOMINATION

'Drarose'.

BACKGROUND OF THE NEW PLANT

The present invention comprises a new and distinct cultivar of snapdragon, botanically known as *Antirrhinum hybrida*, and hereinafter referred to by the cultivar name 'Drarose'. The new cultivar is asexually reproduced from vegetative cuttings and tissue culture resulting from the cross of the seed/pod parent CF1-26, an unnamed and unpatented pink proprietary line and the pollen parent CF1-10, an unnamed and unpatented bronze proprietary line.

'Drarose' is a product of a planned breeding program intended to create new snapdragon cultivars with rose colored flowers, dark green foliage, vigorous growth and basal branching.

The new cultivar was created in 2000 in Gilroy, Calif. and has been asexually reproduced repeatedly by vegetative cuttings and tissue culture in Gilroy, Calif. over a one year period. It has also been trialed at Gilroy, Calif.; Litchfield, Mich. and Andijk, The Netherlands. It has been found to retain its distinctive characteristics through successive propagations; and this novelty is firmly fixed.

DESCRIPTION OF PHOTOGRAPH

This new snapdragon plant is illustrated by the accompanying photograph which shows blooms, buds, and foliage of the plant in full color, the colors shown being as true as can be reasonably obtained by conventional photographic procedures.

FIG. 1 shows the mature inflorescence.

DESCRIPTION OF THE NEW CULTIVAR

The following detailed descriptions set forth the distinctive characteristics of 'Drarose'. The data which defines these characteristics were collected from asexual reproductions by tissue culture or vegetative cuttings carried out in Gilroy, Calif. The plant history was taken on 19–21 week old plants grown in 8 inch pots, blossomed under natural light in a greenhouse and color readings were taken in the greenhouse in Gilroy, Calif. Color references are primarily to The R.H.S. Colour Chart of The Royal Horticultural Society of London (R.H.S.).

THE PLANT

Classification:
*Botanical.*—*Antirrhinum hybrida.*
*Commercial.*—Snapdragon.
Form: Low trailing annual, decumbent.
Growth and branching habit: Vigorous growing, basal branching.
Height: From soil level to top of plant: 10–12 cm without racemes; 12–17 cm with racemes.
Width: 29–33 cm without racemes; 38–40 cm with racemes.
Time to produce a finished flowering plant: 12 weeks.
Outdoor plant performance: Semi-shade, suitable for containers or hanging baskets, as annuals.
Time to initiate roots: Approximately 9 days in the greenhouse.
Time to develop roots: Approximately 18 days in the greenhouse.
Root description: Fibrous, fleshy, white.

THE LEAVES

Arrangement: Opposite on stems and alternate on peduncles.
Length: 2.7–3.0 cm.
Width: 1.1–1.2 cm.
Leaf blade shape: Lanceolate/oblong.
Leaf margin: Entire.
Apex aspect: Acute.
Base aspect: Cuneate.
Texture: Pilose.
Venation: Palmate, green RHS 143A.
Color:
*Upper side.*—Green RHS 147A.
*Under side.*—Green RHS 137B.
Petiole length: 0.7 cm.
Petiole diameter: 0.1 cm.
Petiole color: Green RHS 143A.
Petiole texture: Glandular hairs.

THE STEM

Length including peduncle: 14–19 cm.
Diameter: 0.2–0.35 cm.
Internode length: 1.5–1.6 cm.

Color: Green RHS 137C.
Texture: Pilose.
Anthocyanin: None.

THE BUD

Shape: Obovate.
Diameter: 0.7–0.8 cm.
Length: 1.2–1.5 cm.
Color at tight bud: Light red RHS 48A.

THE FLOWER

Blooming habit: Continuous throughout the growing season.
Period of time to produce a flowering plant: 12 weeks in the greenhouse.
Inflorescence type: Terminal raceme.
Racemes per plant: 37–45 in the greenhouse.
Flowers per raceme: 5–12 in the greenhouse.
Peduncle length: 7.5–10.0 cm.
Peduncle diameter: 0.15 cm.
Peduncle color: Green RHS 138B.
Peduncle texture: Pilose and glandular hairs of the same size.
Raceme length: 5.0–6.0 cm.
Raceme diameter: 0.15 cm.
Raceme texture: Glandular hairs.
Pedicel length: 0.3–0.4 cm.
Pedicel diameter: 0.1 cm.
Pedicel color: Green RHS 143C.
Pedicel texture: Glandular hairs.
Flower form: Gametopetalous, bilabiate, upper lip erect with 2 broad lobes; lower lip with elevated palate and 3 lobes spreading.
Flower size:
*Height.*—2.6–2.9 cm.
*Width.*—1.3–1.5 cm.
*Length.*—3.4–3.6 cm.
Lip color: Upper lip light red RHS 54A (both surfaces); Lower lip light red RHS 54A (both surfaces).
Palate color: Light red RHS 54A with a small spot of yellor RHS 7A.
Throat color: Outside is light red RHS 54C; Inside is light red RHS 54A veination, hairs yellow RHS 6A.
Outer throat texture: Glandular hairs.
Number of lips: Bilabiate.
Lip size: Upper lip size (2 lobes) 1.2–1.5 cm length; 2.3–2.5 cm width; Lower lip size (3 lobes) is 1.5–1.6 cm length; 2.0–2.2 cm width. Base is fused.
Lip margin: Entire.
Lip upper texture: Papillose.
Sepals: 5, base fused.
Sepal length: 0.5–0.6 cm.
Sepal width: 0.25–0.3 cm.
Sepal shape: Lanceolate/oblong; Margin is entire.
Sepal apex: Acute.
Sepal color: Green RHS 143B on upper and lower surfaces.
Sepal texture: Glandular hairs.
Lastingness of individual blooms: 10–12 days in greenhouse environment.
Fragrance: Hint of rose.

THE REPRODUCTIVE ORGANS

Stamens: 4, not fused; filament color and length 2 at 1.4 cm and pink RHS 68B and 2 at 1.9 cm and pink RHS 65C; 8 anthers yellow RHS 6A.
Pollen amount and color: Moderate, yellow RHS 14A.
Pistil: 1 slightly recurved at stigma 1.8 cm; style length is 1.4 cm; color is pink RHS 68B; stigma color is green RHS 145B.
Fruit seed set: Approximately 100 seeds/pod; 1 mm round size; color is grey-purple RHS 186A.

DISEASE AND INSECT RESISTANCE

No susceptibility to diseases or insects noted to date.

COMPARISON WITH KNOWN CULTIVARS

When the instant plant is compared to Luminaire Pink (not patented) the 'Drarose' foliage is longer and narrower while Luminaire Pink is more elliptic/lanceolate. Additionally flowers of 'Drarose' is a deeper rose color than flowers of Luminaire Pink.

Drarose differs from the female parent (CF1-39) (not patented) in numerous ways such as: 1) Drarose is a different color; Drarose has a rose colored flower while CF1-26 is a pink flower. 2) Drarose has a more prostrate habit than CF1-26. 3) Drarose is a more vigorous plant than CF1-26.

Drarose differs from the pollen parent CF1-10 (not patented) in numerous ways such as: 1) Drarose has a rose colored flower while CF1-10 has a bronze flower. 2) Drarose has a darker green leaf than CF1-10. 3) Drarose has a larger flower size than CF1-10.

I claim:

1. A new and distinct snapdragon plant as shown and described herein.

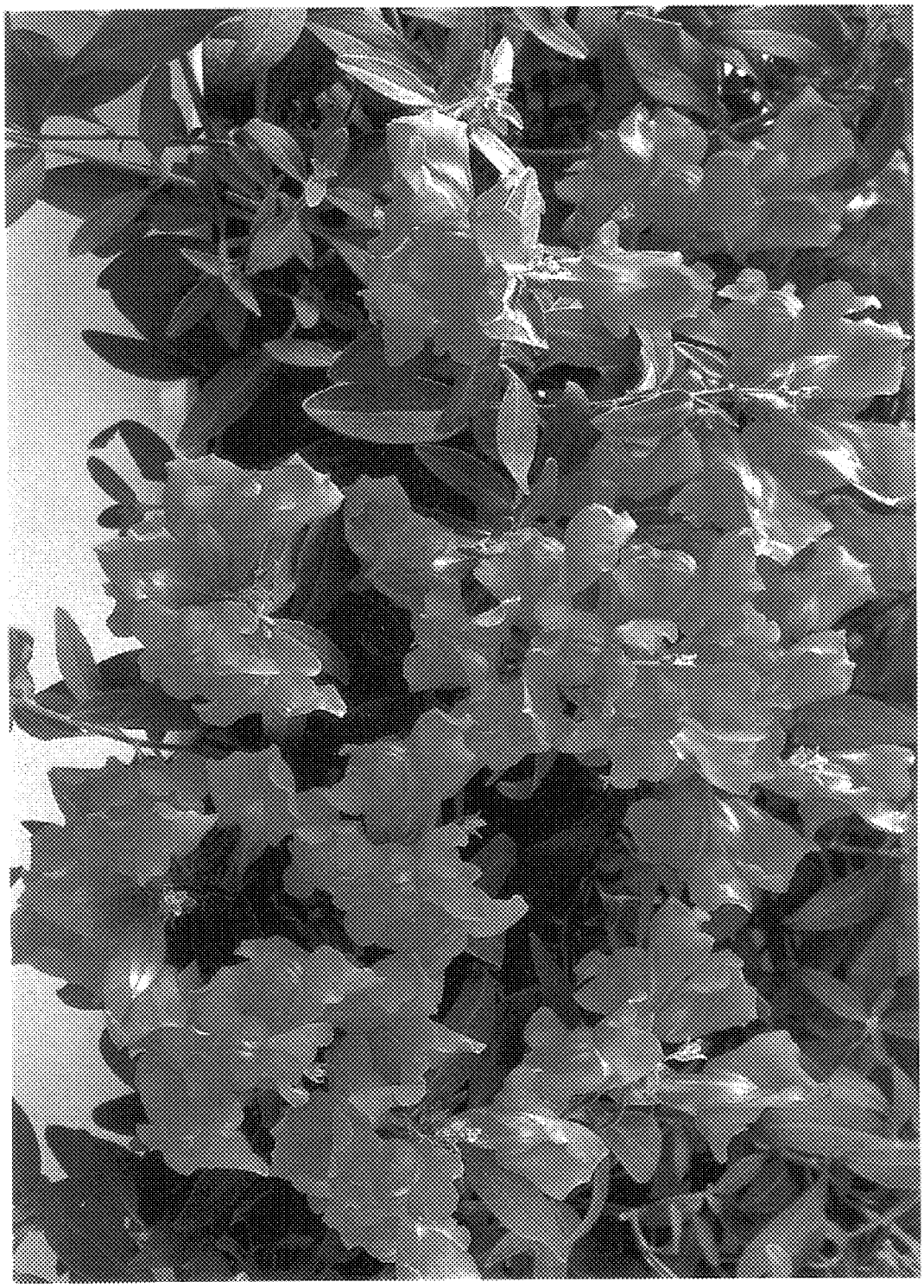

* * * * *